US008304762B2

(12) United States Patent  (10) Patent No.: US 8,304,762 B2
Mori et al.  (45) Date of Patent: Nov. 6, 2012

(54) TETRATHIAFULVALENE DERIVATIVES AND ORGANIC THIN-FILM TRANSISTOR

(75) Inventors: Takehiko Mori, Tokyo (JP); Masato Kanno, Tokyo (JP)

(73) Assignees: Tokyo Institute of Technology, Tokyo (JP); Nissan Chemical Industries, Ltd., Tokyo (JP)

( * ) Notice: Subject to any disclaimer, the term of this patent is extended or adjusted under 35 U.S.C. 154(b) by 553 days.

(21) Appl. No.: 12/551,229

(22) Filed: Aug. 31, 2009

(65) Prior Publication Data

US 2010/0213444 A1    Aug. 26, 2010

(30) Foreign Application Priority Data

Feb. 24, 2009 (JP) ................. 2009-040627

(51) Int. Cl.
*H01L 51/30* (2006.01)
*C07D 339/06* (2006.01)
(52) U.S. Cl. ............ 257/40; 428/690; 428/917; 549/32; 257/E51.047
(58) Field of Classification Search .................. None
See application file for complete search history.

(56) References Cited

U.S. PATENT DOCUMENTS

2003/0105365 A1*  6/2003  Smith et al. .................. 568/774

FOREIGN PATENT DOCUMENTS

| JP | 2004-288836 A | 10/2004 |
|----|---------------|---------|
| JP | 2005-223175 A | 8/2005 |
| JP | 2006-245131 A | 9/2006 |
| JP | 2007-42717 A | 2/2007 |
| JP | 2008-094781 A | 4/2008 |

OTHER PUBLICATIONS

Machine translation of JP2005-223175. Date of publication: Aug. 18, 2005.*
Kanno et al. "Stabilization of organic field-effect transistors in hexamethylenetetrathiafulvalene derivatives substituted by bulky alkyl groups" Journal of Materials Chemistry 2009, 19, 6548-6555. Date of online publication: Jul. 13, 2009.*
Takahashi et. al., "High Mobility Organic Field-Effect Transistor Based on Hexamethylenetertathiafulvalene With Organic Metal Electrodes" Chem. Mater., vol. 19, Sep. 19, 2007, pp. 6382-6384.
Tanemura et. al., "A Mild and Effiecient Procedure for α-Bromination of Ketones Using N-Bromosuccinimide Catalysed by Ammonium Acetate", Chem. Commun., Jan. 28, 2004 pp. 470-471.
Niederl et. al., "The Synthesis of Long Chain Substituted Isocyclics and Similarly Substituted Adipic Acids. The Preparation of α-T-Octycyclohexanone and a Method of Indirect Structure Proof for Ortho and Para Alkylphenols",The Chemical Laboratory of Washington Square College of New York University, Jan. 14, 1936, vol. 59, pp. 717-718.
Renz et. al., "Ketonic Decarboxylation Catalysed by Weak Bases and Its Application to an Optically Pure Substrate", Eur. J. Org. Chem, 2004, pp. 2036-2039.
Engler et. al., "Organic Metals. Systematic Molecular Modifications of Hexamethylenetetraheterofulvalene Donors", IBM Thomas J. Watson Research Journal of the American Chemical Society, vol. 100, No. 12, Jun. 7, 1978, pp. 3769-3776.

* cited by examiner

*Primary Examiner* — Lynda Salvatore
*Assistant Examiner* — Andrew K Bohaty
(74) *Attorney, Agent, or Firm* — Birch, Stewart, Kolasch & Birch, LLP

(57) ABSTRACT

To provide an organic semiconductor of tetrathiafulvalene derivative and an organic thin-film transistor formed therefrom, the tetrathiafulvalene derivative being readily formed into a stable thin film and the organic thin-film transistor having a high mobility and being driven at a low threshold voltage, an organic semiconductor includes a hexamethylenetetrathiafulvalene compound represented by the formula (1) below, and an organic thin-film transistor having a thin film obtained therefrom (where $R^1$ and $R^2$ each independently denote an alkyl group which may have a C1-10 branched structure).

10 Claims, 4 Drawing Sheets

TETRATHIAFULVALENE DERIVATIVES AND ORGANIC THIN-FILM TRANSISTOR

CROSS-REFERENCE TO RELATED APPLICATION

This non-provisional application claims priority under 35 U.S.C. §119(a) on Patent Application No. 2009-040627 filed in Japan on Feb. 24, 2009, the entire contents of which are hereby incorporated by reference.

TECHNICAL FIELD

The present invention relates to an organic semiconductor and an organic thin-film transistor. More particularly, the present invention relates to an organic semiconductor of tetrathiafulvalene derivative and an organic thin-film transistor formed therefrom.

BACKGROUND ART

It has been common practice to use amorphous silicon or polysilicon as the semiconducting material for thin-film transistors.

These inorganic semiconducting materials typified by silicon materials need high-temperature treatment when they are made into thin film. Therefore, they cannot be applied to plastic substrates. Moreover, they need vacuum processing, which requires expensive equipment and hence leads to high production cost.

A new material has recently appeared which is expected to overcome the above-mentioned disadvantage of inorganic semiconducting materials. It is the organic semiconducting material, which is attracting general attention.

Replacing inorganic semiconducting materials with organic ones realizes large area devices easily and economically; it also makes it possible to form devices on a plastic film, thereby giving rise to flexible devices. Flexible devices will realize electronic paper. For example, newspaper in the form of flexible display will greatly reduce the consumption of paper and hence reduce the load on environment.

Applications of organic semiconducting materials which are currently under active investigation include thin-film transistors based on tetrathiafulvalene derivatives (see JP-A 2004-288836, JP-A 2006-245131, JP-A 2005-223175, JP-A 2007-42717, and JP-A 2008-94781, and Chem. Mater., 19, 6382, 2007 (hereinafter referred to as Non-Patent Document 1)).

Noticeable among these derivatives is hexamethylene-tetrathiafulvalene (HMTTF for short hereinafter), which reportedly exhibits as high mobility as 11.2 $cm^2/Vs$ measured in the form of single-crystal transistor (see Non-Patent Document 1).

Unfortunately, this HMTTF possesses the strong donor property and three-dimensional mutual action and hence it merely gives rise to a thin film with unstable film quality. The transistor made from it is poor in characteristic properties.

SUMMARY OF THE INVENTION

The present invention was completed in view of the foregoing. It is an object of the present invention to provide an organic semiconductor of tetrathiafulvalene derivative and an organic thin-film transistor formed therefrom, the tetrathiafulvalene derivative being readily formed into a stable thin film and the organic thin-film transistor having a high mobility and being driven at a low threshold voltage.

In order to achieve the above-mentioned objects, the present inventors conducted a series of researches which led to the finding that HMTTF with specific alkyl groups introduced thereinto gives rise to a thin film which is improved in stability and other properties and that the thin film can be applied to a high-performance organic thin-film transistor which has a high mobility and works at a low threshold voltage. The present invention is based on this finding.

The gist of the present invention resides in the following.

1. An organic semiconductor including a hexamethylenetetrathiafulvalene compound represented by the formula (1) below (1)

(where $R^1$ and $R^2$ each independently denote an alkyl group which may have a C1-10 branched structure).

2. The organic semiconductor as defined in Paragraph 1 above, wherein $R^1$ and $R^2$ each independently denote an alkyl group which has a C3-10 branched structure.

3. A thin film containing the organic semiconductor as defined in Paragraph 1 or 2 above.

4. An organic thin-film transistor having the organic semiconductor thin film as defined in Paragraph 3 above.

5. The organic thin-film transistor as defined in Paragraph 4 above, which has an organic semiconductor layer, a gate electrode placed on the organic semiconductor layer, with a gate insulating layer interposed between them, a source electrode and a drain electrode which are arranged opposite to each other, with the organic semiconductor layer interposed between them, the organic semiconductor layer being formed from the organic semiconductor thin film as defined in Paragraph 3 above.

6. A hexamethylenetetrathiafulvalene compound represented by the formula (1) below (1)

(where $R^1$ and $R^2$ each independently denote an alkyl group which may have a C2-10 branched structure).

7. The hexamethylenetetrathiafulvalene compound as defined in Paragraph 6 above, wherein $R^1$ and $R^2$ each independently denote an alkyl group which has a C3-10 branched structure.

ADVANTAGEOUS EFFECTS OF INVENTION

The organic semiconductor according to the present invention is composed of tetrathiafulvalene molecules modified with specific alkyl chains, so that it gives rise to a thin film having greatly improved film quality.

This organic semiconductor has the tetrathiafulvalene skeleton, so that it gives rise to an organic thin film transistor having a higher mobility than conventional ones based on oligothiophene or polythiophene.

DESCRIPTION OF EMBODIMENTS

The following is a detailed description of the present invention.

The organic semiconductor according to the present invention includes a hexamethylenetetrathiafulvalene compound represented by the formula (1) below (1)

where $R^1$ and $R^2$ each independently denote an alkyl group which may have a C1-10 branched structure.

In the formula (1) above, no specific restrictions are imposed on the alkyl group which may have a C1-10 branched structure. It includes, for example, methyl group, ethyl group, n-propyl group, i-propyl group, n-butyl group, s-butyl group, t-butyl group, n-pentyl group, 1-methylbutyl group, 2-methylbutyl group, 3-methylbutyl group, 1,1-dimethylpropyl group, 2,2-dimethylpropyl group, n-hexyl group, 1-methylpentyl group, 2-methylpentyl group, 1,1-dimethylbutyl group, 1-ethylbutyl group, 1,1,2-trimethylpropyl group, n-heptyl group, n-octyl group, 2-ethylhexyl group, n-nonyl group, and n-decyl group.

Of these examples, the following are preferable because they lower the drive voltage of the organic thin-film transistor and increase the electron mobility. i-propyl group, s-butyl group, t-butyl group, 1-methylbutyl group, 2-methylbutyl group, 3-methylbutyl group, 1,1-dimethylpropyl group, 2,2-dimethylpropyl group, 1-methylpentyl group, 2-methylpentyl group, 1,1-dimethylbutyl group, 1-ethylbutyl group, 1,1,2-trimethylpropyl group, and 2-ethylhexyl group. They have a C3-10 branched structure. Preferable among the foregoing examples is t-butyl group.

The alkylated HMTTF compound represented by the formula (1) above can be produced by combination of known reactions.

To be specific, it can be produced by a series of reactions as represented in the following scheme according to the process described in Chem. Commun., 470 (2004), J. Am. Chem. Soc., 59, 717 (1937), Eur. J. Org. Chem., 2036 (2004), etc. They are not limitative.

The alkylated HMTTF compound explained above can be made into thin film suitable for use as the semiconductor layer constituting semiconductor devices such as field effect transistors, light-emitting diodes, photoelectric conversion elements, and organic thin-film solar cells.

Incidentally, no specific restrictions are imposed on the method for forming the thin film containing the organic semiconductor of the present invention. Any known conventional methods can be used, which include vacuum deposition and application by casting, dipping, spin coating, etc. with a varnish containing the semiconductor dissolved in an organic solvent.

The semiconductor layer is not specifically restricted in thickness. An adequate thickness is 1 nm to 10 μm, preferably 10 nm to 500 nm.

The above-mentioned semiconductor element is unique in being formed from the foregoing alkylated HMTTF as the semiconductor. It may have other constituents selected from any known ones.

The following is a description of a field effect transistor as an example of the semiconductor element.

The field effect transistor is usually composed of an organic semiconductor layer, a gate electrode placed thereon, with a gate insulating layer interposed between them, and a source electrode and a drain electrode which are arranged opposite to each other, with an organic semiconductor layer interposed between them. According to the present invention, the organic semiconductor layer is formed from the organic semiconductor thin film containing the above-mentioned alkylated HMTTF.

The type of the field effect transistor is not specifically restricted. It may include bottom gate/bottom contact type, bottom gate/top contact type, and top gate/bottom contact type. Each type requires its own arrangement of the foregoing gate electrode, gate insulating layer, source electrode, drain electrode, and organic semiconductor layer.

The field effect transistor is formed on a substrate, which is selected from silicon substrate, glass substrate, and plastic substrate (such as polyethylene terephthalate).

The gate electrode is formed from any of p-doped silicon, n-doped silicon, indium-tin oxide (ITO), conductive polymer (such as doped polythiophene and polyaniline), and metal (such as gold, silver, platinum, and chromium).

The gate insulating layer may be formed from any of inorganic compounds (such as silicon oxide, silicon nitride, aluminum oxide, aluminum nitride, and tantalum oxide) and organic compounds (such as polyvinyl alcohol, polyvinyl phenol, polymethyl methacrylate, and cyanoethyl pullulan).

The source and drain electrodes may be formed from any of gold, silver, platinum, chromium, aluminum, indium, alkali metal (such as Li, Na, K, Rb, and Cs), and alkaline earth metals (such as Mg, Ca, Sr, and Ba).

Incidentally, the organic semiconductor layer may be composed of not only the alkylated HMTTF compound of the present invention but also any crystalline organic semiconducting material as an electron donor in an adequate amount, which includes polycyclic aromatic material (such as pentacene, tetracene, anthracene, perylene, pyrene, coronene, chrysene, decacyclene, and violanthrene); phthalocyanine, triphenylene, thiophene oligomer, and derivatives thereof; and tetrathiafulvalenes such as dibenzotetrathiafulvalene, tetrathiotetracene, and regioregular poly(3-alkylthiophene).

EXAMPLES

The present invention will be described in more detail with reference to the following Examples and Comparative Examples, which are not intended to restrict the scope thereof.

Data in these examples were obtained by using the instruments listed below.

For EI-MS Spectrum:
  Gas chromatograph mass spectrometer (QP-5000, made by Shimadzu Corp.)
For IR Spectrum:
  Fourier transform infrared spectrophotometer (FTIR-8400S, made by Shimadzu Corp.), by KBr pellet method.
For $^1$H-NMR Spectrum:
  Nuclear magnetic resonance apparatus (JNM-AL300, made by Nippon Denshi Co., Ltd.), which employs CDCl$_3$ as the solvent (internal standard TMS).

For Surface Observation:
  AFM (made by Seiko Instruments Co., Ltd.), which employs SPA-300/SPI3800 probe system and a cantilever of Si3N4.
For XRD: X-Ray Diffractometer for Analyzing Crystallinity of Thin-Film Material (X' Pert-Pro-MRD).

[1] Synthesis of β-alkyl HMTTF

Comparative Example 1

Synthesis of HMTTF (1)

In 40 mL of acetone was dissolved 2.4 g or 20 mmol of 2-chlorocyclopentanone (1a). To the resulting solution was added little by little 8.7 g or 50 mmol of potassium isopropylxanthate, followed by stirring for an hour. The resulting yellowish suspension underwent suction filtration and the filtrate was freed of acetone by using an evaporator. Thus there was obtained an ocher oily compound (1b).

MS (EI): m/z 218 (M$^+$).

The compound (1b) obtained in the foregoing step was slowly added dropwise to 15 mL of conc. sulfuric acid at 0° C. After stirring for an hour, the solution was dropped onto about 20 g of ice. The resulting light yellowish suspension was filtered off, and the separated solid was dissolved in a 1:1 (v/v) mixture of hexane and dichloromethane. The resulting solution was passed through a silica gel column. A nearly colorless band was recovered from the initial eluate. Thus there was obtained 2.3 g or 14.4 mmol of white solid compound (1c). Yield=72%.

MS (EI): m/z 158 (M$^+$).

The compound (1c) in an amount of 2.3 g or 14.4 mmol, incorporated with 3 mL of trimethyl phosphite, was refluxed for 12 hours under nitrogen. After cooling to room temperature, the reaction product (diluted with methanol) was filtered off by suction. The resulting solids were recrystallized from toluene. Thus there was obtained 1.7 g or 6.1 mmol of HMTTF (1) in the form of yellowish dendroid crystals. Yield=85%. This is a known substance.

MS (EI): m/z 284 (M$^+$).
$^1$H-NMR: δ2.32-2.46 (m, 4H), 2.47-2.58 (m, 8H).
IR: 1453, 1610, 2907 cm$^{-1}$.

Example 1

Synthesis of β-MeHMTTF (2)

In 10 mL of diethyl ether were dissolved 5.0 g or 51 mmol of 3-methylcyclopentanone (2a), 9.3 g or 52 mmol of N-bromosuccinimide (NBS), and 0.39 g or 5.0 mmol of ammonium acetate, followed by stirring for five hours. The resulting light yellowish solution was filtered off, and the filtrate was given diethyl ether and water. After separation into two layers, the diethyl ether layer was freed of diethyl ether by using an evaporator. Thus there was obtained a yellowish oily compound (2b).

MS (EI): m/z 176 (M$^+$).

The compound (2b) was dissolved in 40 mL of acetone and the resulting solution was added little by little to 8.7 g or 50 mmol of potassium isopropylxanthate, followed by stirring for an hour. The resulting yellowish brown suspension was filtered off, and the filtrate was freed of acetone by using an evaporator. Thus there was obtained a yellowish brown oily compound (2c).

MS (EI): m/z 232 (M$^+$).

The compound (2c) was slowly added dropwise to 10 mL of ice-cooled conc. sulfuric acid. After stirring for an hour, the solution was dropped onto about 40 g of ice. There was obtained a milky white suspension. From this suspension was extracted with dichloromethane the desired organic matter, which was subsequently washed with distilled water, dried with magnesium sulfate, and freed of dichloromethane by using an evaporator. Thus there was obtained a light yellowish oily compound (2d).

MS (EI): m/z 172 (M$^+$).

The compound (2d) was given 3 mL of triethylphosphite, followed by reaction at 130° C. for 12 hours under nitrogen. The resulting reaction liquid was given methanol to yield yellowish solids, which were filtered out and recrystallized four times from ethanol. Thus there was obtained 0.081 g or 0.26 mmol of β-MeHMTTF (2) in the form of yellowish needle crystal, which is a known substance. Yield=1.1%.

m.p. 130° C.

MS (EI): m/z 312 (M$^+$).

$^1$H-NMR: δ1.16-1.19 (d, 6H), 1.50-3.00 (m, 10H).

IR: 1460, 1607, 2905 cm$^{-1}$.

Incidentally, it is known from the $^1$H-NMR data described in J. Am. Chem. Soc., 100, 3769 (1978) that HMTTF having a methyl group at the β position has an absorption peak near δ=1.16 and HMTTF having a methyl group at the α position has an absorption peak near δ=1.10. The MeHMTTF before recrystallization was found by $^1$H-NMR to be a mixture in which α:β=2:1. It was also found that recrystallization repeated four times gave a sample which showed no peak near δ=1.10 and which was composed solely of β form and superior in crystallinity.

It is considered that other alkyl-substituted compounds were also separated into isomers in the same way as above and the β form was separated as the least soluble isomer.

Example 2

Synthesis of β-tBuHMTTF (3)

To 29.9 g or 148 mmol of compound (3a) was added 0.45 g or 4 mmol of sodium carbonate, followed by stirring at 300° C. for two hours. The desired product, which resulted from the reaction, and water were recovered by distillation, and water was discarded. Thus there was obtained 19.3 g or 138 mmol of compound (3b). Yield=93%.

MS (EI): m/z 140 (M+).

In 30 mL of diethyl ether were dissolved 4.6 g or 33 mmol of compound (3b), 6.2 g or 35 mmol of NBS, and 0.25 g or 3.3 mmol of ammonium acetate, followed by stirring for three hours. The resulting colorless solution was filtered off, and the filtrate was given water. After separation into two layers, the diethyl ether layer was freed of diethyl ether by using an evaporator. Thus there was obtained 4.6 g or 21 mmol of yellowish oily compound (3c). Yield=65%.

MS (EI): m/z 218 (M+).

In 40 mL of acetone was dissolved 4.6 g or 21 mmol of compound (3c). To the resulting solution was added little by little 6.3 g or 36 mmol of potassium isopropylxanthate, followed by stirring for an hour. The resulting yellowish brown suspension was filtered off, and the filtrate was freed of acetone by using an evaporator. Thus there was obtained 5.5 g or 20 mmol of yellowish brown oily compound (3d). Yield=96%.

MS (EI): m/z 274 (M+).

The compound (3d) in an amount of 5.5 g or 20 mmol was slowly added dropwise to 10 mL of ice-cooled conc. sulfuric acid. After stirring for an hour, the solution was dropped onto about 40 g of ice. There was obtained a milky white suspension. From this suspension was extracted with dichloromethane the desired organic matter, which was subsequently washed with distilled water, dried with magnesium sulfate, and the resulting solid was dissolved in a 1:1 (v/v) mixture of hexane and dichloromethane. The resulting solution was passed through a silica gel column. A light yellowish band was recovered from the initial eluate. Thus there was obtained 2.2 g or 10 mmol of yellowish oily compound (3e). Yield=50%.

MS (EI): m/z 214 (M+).

$^1$H-NMR: δ0.93 (s, 9H), 2.49-2.84 (m, 5H).

To 0.64 g or 3.0 mmol of compound (3e) was given 3 mL of triethylphosphite, followed by stirring at 130° C. for 12 hours under nitrogen. To the reaction product was added methanol, and the resulting solution was filtered out. The separated solids were recrystallized repeatedly from toluene and benzonitrile. Thus there was obtained 0.29 g or 0.73 mmol of β-tBuHMTTF (3) in the form of slightly soluble yellowish flaky crystals. Yield=48%.

m.p. 240° C.

MS (EI): m/z 396 (M+).

$^1$H-NMR: δ0.82-0.98 (s, 18H), 2.25-2.47 (m, 8H), 2.62-2.77 (m, 2H).

IR: 1463, 1611, 2900 cm$^{-1}$.

Example 3

Synthesis of β-nPeHMTTF (4)

To 40 mL of 70% nitric acid (heated at 110° C.) were added under nitrogen 0.12 g or 1.0 mmol of ammonium vanadate and 0.17 g or 1.0 mmol of 1-hydroxy-4-n-pentylcyclohexane (4a). After stirring for a while, the solution was transferred to an oil bath at 60° C., and 10.1 g or 59 mmol of 1-hydroxy-4-n-pentylcyclohexane (4a) was further added, followed by stirring for an hour. The reaction product was diluted with water, and the desired product was extracted with diethyl ether. The extract was freed of diethyl ether by using an evaporator. Thus there was obtained 12.1 g or 56.0 mmol of white solid compound (4b). Yield=93%.

To 12.1 g or 56.0 mmol of compound (4b) was added 0.21 g or 2 mmol of sodium carbonate, followed by stirring at 300° C. for two hours. The desired product and water were recovered by distillation and the distillate was freed of water. Thus there was obtained 5.9 g or 38 mmol of compound (4c). Yield=68%.

MS (EI): m/z 154 (M+).

To 30 mL of diethyl ether were added 5.9 g or 38 mmol of compound (4c), 6.9 g or 39 mmol of NBS, and 0.29 g or 3.8 mmol of ammonium acetate, followed by stirring for three hours. The resulting colorless solution was filtered off. The filtrate was given water for separation. Upon removal of diethyl ether by means of an evaporator, there was obtained 3.8 g or 16 mmol of light yellowish oily compound (4d). Yield=42%.

MS (EI): m/z 232 (M+).

To 3.8 g or 16 mmol of compound (4d) dissolved in 40 mL of acetone was added little by little 6.6 g or 38 mmol of potassium isopropylxanthate, followed by stirring for an hour. The resulting yellowish brown suspension was filtered off and the filtrate was recovered and freed of acetone by means of an evaporator. Thus there was obtained 3.9 g or 13 mmol of yellowish brown oily compound (4e). Yield=84%.

MS (EI): m/z 288 (M+).

The compound (4e) in an amount of 3.9 g or 13 mmol was slowly added dropwise to 10 mL of ice-cooled conc. sulfuric acid. After stirring for an hour, the solution was dropped onto about 40 g of ice. There was obtained a milky white suspension. From this suspension was extracted with dichloromethane the desired organic matter, which was subsequently washed with distilled water, dried with magnesium sulfate, and the resulting solid was dissolved in a 1:1 (v/v) mixture of hexane and dichloromethane. The resulting solution was passed through a silica gel column. A light yellowish band was recovered from the initial eluate. Thus there was obtained 1.6 g or 7.2 mmol of yellowish brown oily compound (4f). Yield=55%.

MS (EI): m/z 228 (M+).

To 1.6 g or 7.2 mmol of compound (4f) was given 3 mL of triethylphosphite, followed by stirring at 130° C. for 12 hours under nitrogen. To the reaction product was added methanol and filtered out. The resulting yellowish solid was recrystallized four times from ethanol. Thus there was obtained 0.47 g or 1.1 mmol of β-nPeHMTTF (4) in the form of yellowish needle crystals. Yield=30%.

m.p. 150° C.

MS (EI): m/z 424 (M+).

$^1$H-NMR: δ0.84-0.95 (t, 6H), 1.20-1.40 (m, 12H), 1.42-1.55 (m, 4H), 1.80-2.90 (m, 10H).

IR: 1458, 1602, 2903 cm$^{-1}$.

Example 4

Synthesis of β-tPeHMTTF (5)

To 40 mL of 70% nitric acid (heated at 110° C.) were added under nitrogen 0.18 g or 1.5 mmol of ammonium vanadate and 0.17 g or 1.0 mmol of 1-hydroxy-4-t-pentylcyclohexane (5a). After stirring for a while, the solution was transferred to an oil bath at 60° C., and 14.9 g or 88 mmol of 1-hydroxy-4-t-pentylcyclohexane (5a) was further added, followed by stirring for an hour. The reaction product was diluted with water, and the desired product was extracted with diethyl ether. The extract was freed of diethyl ether by means of an evaporator. Thus there was obtained 17.7 g or 82 mmol of white solid compound (5b). Yield=92%.

To 17.7 g or 82 mmol of compound (5b) was added 0.27 g or 2.5 mmol of sodium carbonate, followed by stirring at 300° C. for two hours. The desired product and water were recovered by distillation and the distillate was freed of water. Thus there was obtained 6.6 g or 43 mmol of compound (5c). Yield=52%.

MS (EI): m/z 154 (M$^+$).

To 30 mL of diethyl ether were added 6.6 g or 43 mmol of compound (5c), 8.0 g or 45 mmol of NBS, and 0.33 g or 4.3 mol of ammonium acetate, followed by stirring for three hours. The resulting colorless solution was filtered off. The filtrate was given water for separation. Upon removal of diethyl ether by means of an evaporator, there was obtained 7.2 g or 31.0 mmol of light yellowish oily compound (5d). Yield=72%.

MS (EI): m/z 232 (M$^+$).

To 7.2 g or 31.0 mmol of compound (5d) dissolved in 40 mL of acetone was added little by little 7.5 g or 43.0 mmol of potassium isopropylxanthate, followed by stirring for an hour. The resulting yellowish brown suspension was filtered off and the filtrate was recovered and freed of acetone by means of an evaporator. Thus there was obtained 7.8 g or 27.0 mmol of yellowish brown oily compound (5e). Yield=87%.

MS (EI): m/z 288 (M$^+$).

The compound (5e) in an amount of 7.8 g or 27.0 mmol was slowly added dropwise to 10 mL of ice-cooled conc. sulfuric acid. After stirring for an hour, the solution was dropped onto about 40 g of ice. There was obtained a milky white suspension. From this suspension was extracted with dichloromethane the desired organic matter, which was subsequently washed with distilled water, dried with magnesium sulfate, and the resulting solid was dissolved in a 1:1 (v/v) mixture of hexane and dichloromethane. The resulting solution was passed through a silica gel column. A light yellowish band was recovered from the initial eluate. Thus there was obtained 3.2 g or 14.0 mmol of yellowish brown oily compound (5f). Yield=52%.

MS (EI): m/z 228 (M$^+$).

$^1$H-NMR: δ0.80-0.95 (m, 9H), 1.20-1.40 (q, 2H), 2.49-2.84 (m, 5H).

IR: 1454, 1609, 2895 cm$^{-1}$.

To 3.2 g or 14.0 mmol of compound (5f) was given 3 mL of triethylphosphite, followed by stirring at 130° C. for 12 hours under nitrogen. To the reaction product was added methanol and the resulting precipitates were filtered off. After repeated recrystallization from toluene and benzonitrile, there was obtained 1.6 g or 3.8 mmol of β-tPeHMTTF (5) in the form of slightly soluble yellowish flaky crystals. Yield=54%.

m.p. 235° C.

MS (EI): m/z 424 (M$^+$).

$^1$H-NMR: δ0.73-0.94 (m, 18H), 1.11-1.34 (m, 14H, 2.22-2.44 (m, 8H), 2.66-2.85 (m, 2H).

As the result of X-ray analysis of structure, it was found that this substance gives the isolated β form upon recrystallization.

[2] Preparation of Organic Semiconductor Thin Film and Organic Thin-Film Transistor Examples 5 to 8 and Comparative Example 2

Each of the compounds (1) to (5) obtained in Examples 1 to 4 and Comparative Example 1 mentioned above was formed into an organic semiconductor thin film by vacuum deposition on an $SiO_2$ substrate (300 nm) treated with octyltrichlorosilane (OTS). The surface AFM image of the thin film is shown in FIGS. 1 to 5.

FIGS. 1 to 5 indicate the following. The compound (1), which has no substituents, gives a coarse thin film composed of very large grains, while the compounds (2) to (5), each of which has substituents, give a thin film composed of smaller grains. Particularly, the compounds (2) and (4), each of which has bulky substituents, give a thin film which is composed of grains smaller than 1 μm and has a comparatively smooth surface whose roughness is about 3 nm in terms of RMS (root mean square).

The samples of thin film obtained in these examples were examined by out-of-plane XRD for molecular arrangement in the direction perpendicular to the film surface. The samples of thin film prepared from the compounds (2) and (4) give diffraction peaks, as shown in FIGS. 6 and 7.

Figure 1:
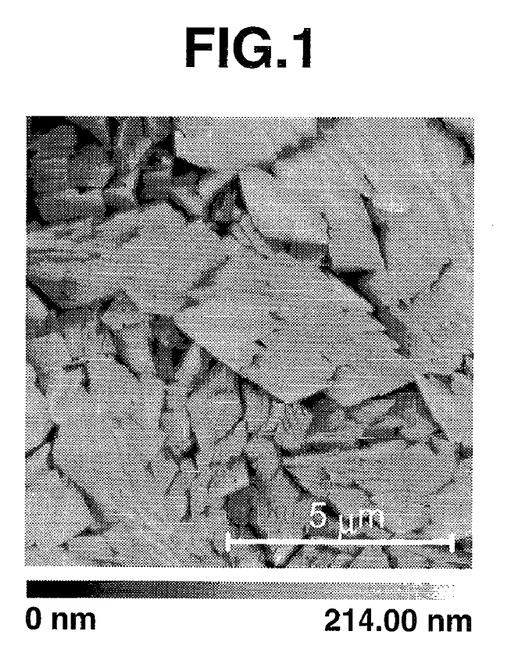
FIG. 1 is a diagram showing the surface AFM image of the organic semiconductor thin film prepared in Comparative Example 2.
Figure 2:
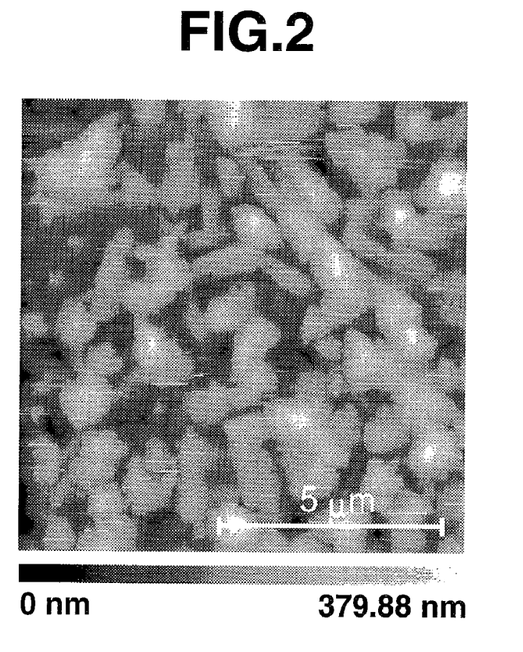
FIG. 2 is a diagram showing the surface AFM image of the organic semiconductor thin film prepared in Example 5.
Figure 3:
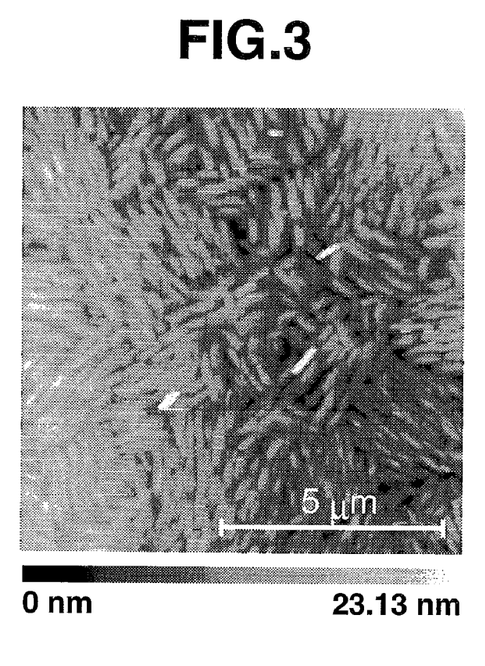
FIG. 3 is a diagram showing the surface AFM image of the organic semiconductor thin film prepared in Example 6.
Figure 4:
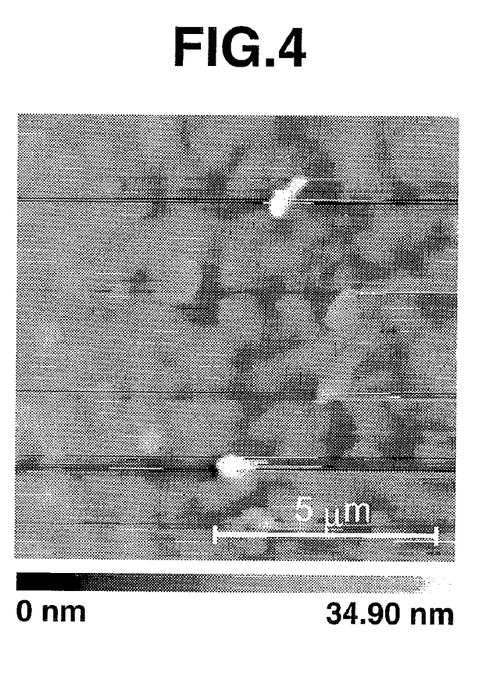
FIG. 4 is a diagram showing the surface AFM image of the organic semiconductor thin film prepared in Example 7.
Figure 5:
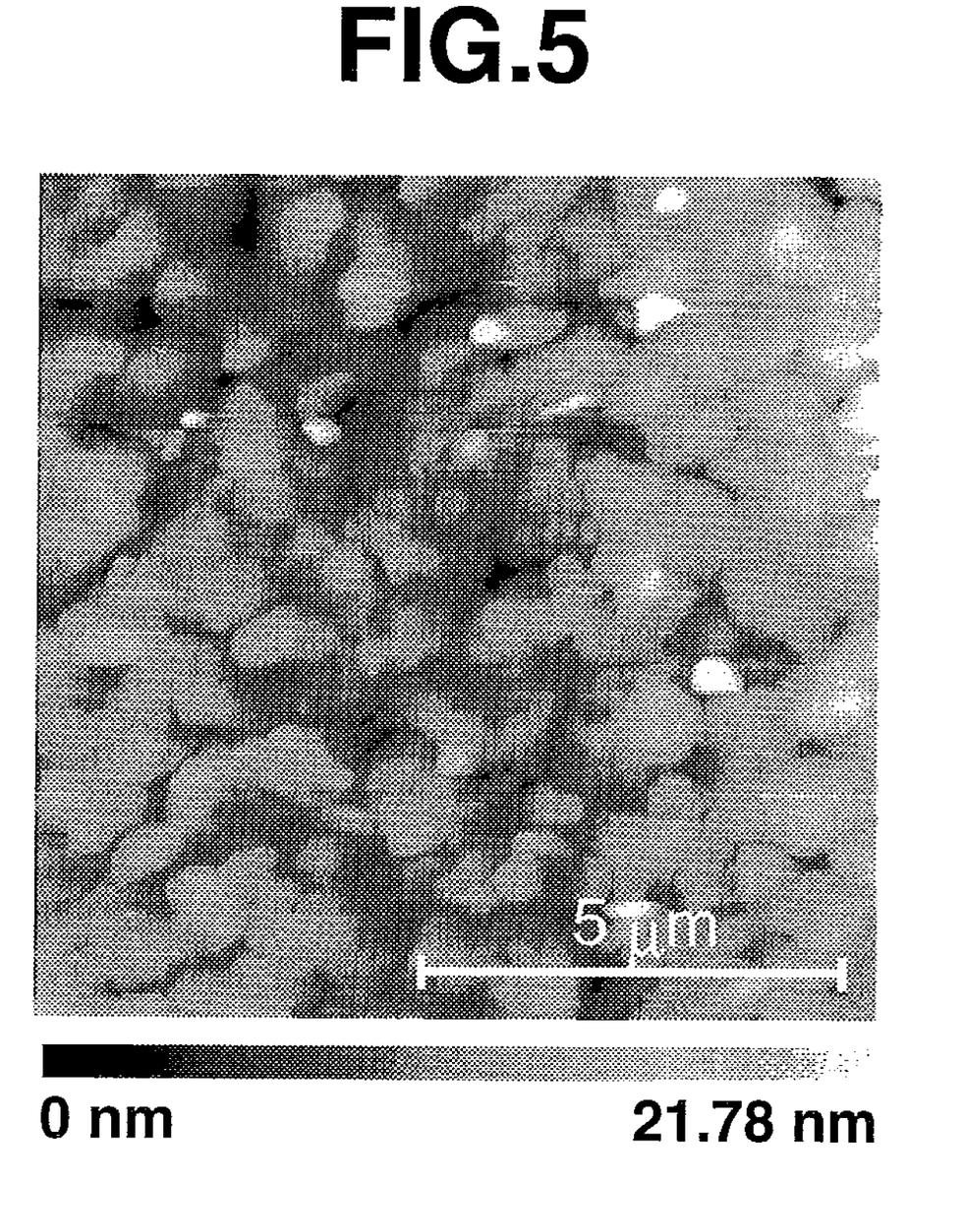
FIG. 5 is a diagram showing the surface AFM image of the organic semiconductor thin film prepared in Example 8.
Figure 6:
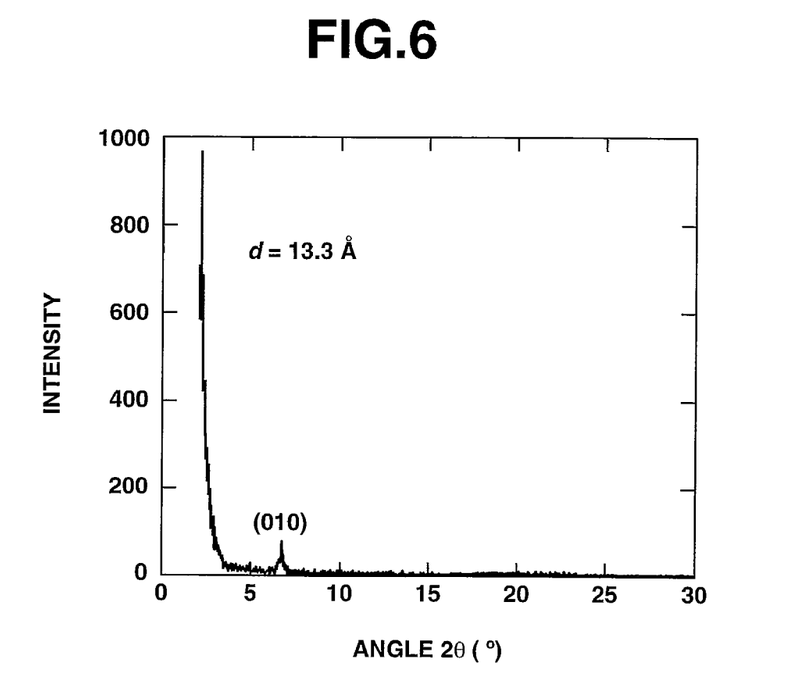
FIG. 6 is a diagram showing the results of XRD measurement of the organic semiconductor thin film prepared in Example 6.
Figure 7:
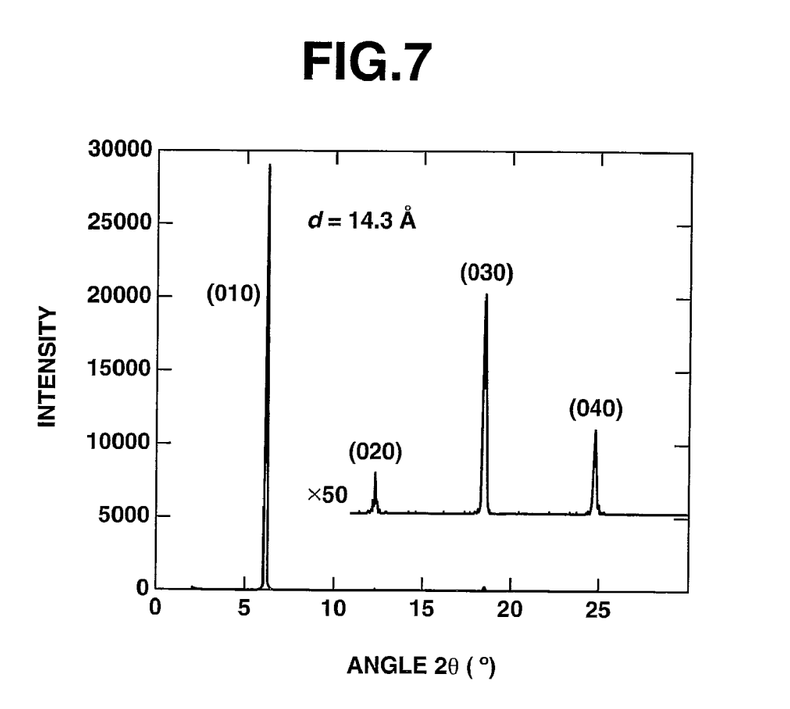
FIG. 7 is a diagram showing the results of XRD measurement of the organic semiconductor thin film prepared in Example 8.

It is noted from FIGS. 6 and 7 that in both samples the surface-to-surface distance (d) calculated from the diffraction peak agrees with the length of the b-axis of single crystal (13.5 Å and 14.4 Å).

This result suggests that the molecules of these compounds grow in the lamellar state, with the ac plane parallel to the substrate.

An organic thin-film transistor of top-contact type was prepared from the organic semiconductor thin film mentioned above by forming thereon electrodes (having a gate width W=1000 μm and a gate length L=100 μm) from gold by vapor deposition.

The following procedure was employed for vacuum deposition to form the semiconductor thin film and gold electrodes. A vapor source and a substrate are placed opposite to each other in a high-vacuum glass chamber. The vapor source is a crucible holding the sample. The degree of vacuum in the glass chamber is $10^{-5}$ Torr (or ca. $1.3 \times 10^{-4}$ Pa). The sample in the crucible is deposited on the substrate by resistance heating.

Each sample of the transistors was tested for voltage-current curve at 25° C. by using an electrometer (Keithley 4200, semiconductor parameter analyzer, made by Keithley Instruments Co., Ltd.). The test includes a step of applying a voltage of −10 to −60 V across the source electrode and the drain electrode, with the gate voltage varied between −30 to −80 V. The results of the test indicate the transistor characteristics (mobility, threshold voltage, and on-off ratio) as shown in Table 1.

Incidentally, the drain current $I_D$ in the saturated state is represented usually by the equation below. In other words, the mobility μ of the organic semiconductor can be obtained from the slope of the graph, with the ordinate representing the square root of the absolute value of the drain current $I_D$ and the abscissa representing the gate voltage $V_G$, $$I_D = WC_\mu (V_G - V_T)^2 / 2L$$

where L: gate length, W: gate width, C: electrostatic capacity per unit area of insulating layer, $V_G$: gate voltage, and $V_T$: threshold voltage.

The on-off ratio was calculated from the ratio of the maximum and minimum drain current values ($I_D$).

TABLE 1

| | Temperature of substrate at the time of vapor deposition (° C.) | Mobility μ (cm²/Vs) | Threshold voltage (V) | On-off ratio |
|---|---|---|---|---|
| Example 5 | 25 | $2.6 \times 10^{-3}$ | 7.6 | $1 \times 10^3$ |
| Example 6 | 50 | 0.98 (0.52*) | −2.1 (+2.99*) | $5 \times 10^5$ ($2 \times 10^{5*}$) |
| Example 7 | 50 | 0.19 | −0.36 | $5 \times 10^4$ |
| Example 8 | 85 | 0.60 | −2.6 | $2 \times 10^5$ |
| Comparative Example 2 | 40 | 3.6 (no FET*) | +27 | $3 \times 10^3$ |

*measured after 85 days.

The alkylated HMTTF (in Examples 5 to 8) gives a good thin film on $SiO_2$ by vapor deposition. Therefore, it is suitable for the organic thin film transistor which maintains good transistor characteristics over a comparatively long period as shown in Table 1.

By contrast, the non-alkylated HMTTF (in Comparative Example 2) gives transistors with inconsistent or unsatisfactory characteristics. Even those samples which show transistor characteristics are inferior to those in Examples 5 to 8, and they do not show the characteristics of field effect transistor after 85 days.

Japanese Patent Application No. 2009-040627 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. An organic semiconductor comprising a hexamethylene-tetrathiafulvalene compound represented by the formula (1) below (1)

$R^1$—[structure]—$R^2$ where $R^1$ and $R^2$ each independently denote an C3-10 straight chain or branched chain alkyl group.

2. The organic semiconductor as defined in claim 1, wherein $R^1$ and $R^2$ each independently denote a C4-10 alkyl group.

3. A thin film containing the organic semiconductor as defined in claim 1 or 2.

4. An organic thin-film transistor having the organic semiconductor thin film as defined in claim 3.

5. The organic thin-film transistor as defined in claim 4, which has an organic semiconductor layer, a gate electrode placed on said organic semiconductor layer, with a gate insulating layer interposed between them, a source electrode and a drain electrode which are arranged opposite to each other, with said organic semiconductor layer interposed between them.

6. A hexamethylenetetrathiafulvalene compound represented by the formula (1) below (1)

where $R^1$ and $R^2$ each independently denote a straight chain or branched chain a C3-10 alkyl group.

7. The hexamethylenetetrathiafulvalene compound as defined in claim 6, wherein $R^1$ and $R^2$ each independently denote an alkyl group which has a C4-10 branched structure.

8. The organic thin-film transistor as defined in claim 4 wherein the organic semiconductor thin film further comprises polycyclic aromatic material, phthalocyanine, phthalocyanine derivative, triphenylene, triphenylene derivative, thiophene oligomer, thiophene oligomer derivative or tetrathiafulvalene.

9. The organic thin-film transistor as defined in claim 8 wherein the polycyclic aromatic material is pentacene, tetracene, anthracene, perylene, pyrene, coronene, chrysene, decacyclene, or violanthrene.

10. The organic thin-film transistor as defined in claim 8 wherein the tetrathiafulvalene is dibenzotetrathiafulvalene, tetrathiotetracene, or regioregular poly(3-alkylthiophene).

* * * * *